United States Patent [19]

Johnson

[11] 4,277,564

[45] Jul. 7, 1981

[54] PREPARING ENTOMOCIDAL PRODUCTS WITH OLIGOSPOROGENIC MUTANTS OF BACILLUS THURINGIENSIS

[75] Inventor: Donovan E. Johnson, Peoria, Ill.

[73] Assignee: The United States of America as represented by the Secretary of Agriculture, Washington, D.C.

[21] Appl. No.: 110,864

[22] Filed: Jan. 9, 1980

[51] Int. Cl.$^3$ ............................................. C12N 3/00
[52] U.S. Cl. .................................. 435/242; 435/172; 435/253; 435/832
[58] Field of Search ................. 435/242, 88, 832, 172, 435/253

[56] References Cited

U.S. PATENT DOCUMENTS 3,578,383  9/1973  Shieh et al. ..................... 435/832 X
4,133,716  1/1979  Zamola et al. ...................... 435/242

OTHER PUBLICATIONS

Yousten, "A Method for the Isolation of Asporogenic Mutants of Bacillus Thuringiensis", Con. J. Microbiology, vol. 24 (1978) pp. 492-494.

Primary Examiner—R. B. Penland
Attorney, Agent, or Firm—M. Howard Silverstein; David G. McConnell; Curtis P. Ribando

[57] ABSTRACT

Six oligosporogenic mutant strains obtained from *Bacillus thuringiensis* subsp. kurstaki yield parasporal products substantially free of interfering spores when cultivated under normal sporulation conditions. These parasporal products have utility in the biological control of pest insects.

9 Claims, No Drawings

PREPARING ENTOMOCIDAL PRODUCTS WITH OLIGOSPOROGENIC MUTANTS OF BACILLUS THURINGIENSIS

BACKGROUND OF THE INVENTION

1. Field of the Invention

With the recent trend toward biological pest control, considerable attention has been given to the insecticidal properties of the bacterium *Bacillus thuringienis*. Of particular interest is the subspecies, kurstaki, because of its broad and effective entomocidal host range. The subspecies is commercially prominent for biological control of lepidopteran pest insects.

The sporulating cells of *B. thuringiensis* each produce a spore (endospore) and a diamond-shaped proteinaceous crystal (paraspore or inclusion body). The entomocidal properties have been attributed solely to the δ-endotoxin which is a major component of the parasporal crystal. When the crystal solubilizes in the insect gut, it gives rise to a protoxin which is activated by proteolytic digestion.

At the completion of sporulation, the autolyzing cells release both the spores and the crystals into the culture medium. For most investigative research purposes, it is desirable that the latter be recovered in a substantially pure state. Also, environmental considerations dictate that commercial insecticidal preparations be substantially free of viable spores. However, the similarity in size and density renders separation of the crystals and spores both complicated and laborious. This invention relates to a method for the production of parasporal products which simplifies, or even obviates, such a separation.

2. Description of the Prior Art

It had been known from the teachings of Shieh et al., U.S. Pat. No. 3,758,383, that it was possible to select a mutant strain of *B. thuringiensis* which could be cultured under sporulation conditions without the usual production of the crystal bodies. Attempts at the reverse situation have led to reports of other mutants which fail to sporulate but which do form the crystalline paraspores. NishiitsutsujiUwo et al. [J. Invert. Path. 25: 355-361 (1975)] shows the selection of five completely asporogenous strains from mutagenized wild types. Two of these were derived from the subspecies kurstaki, but overall were somewhat less toxic than the parent strain. Other attempts to mutate *B. thuringiensis* have led to strains which produce neither spores nor crystals [A. A. Yousten, Can. J. Microbiol. 24: 492-494 (1978)].

SUMMARY OF THE INVENTION

I have now discovered six oligosporogenic mutant strains of *B. thuringiensis*, subspecies kurstaki, capable of producing parasporal products which are substantially free of contaminating spores and which yield activated protein having toxigenic activity equal to or greater than that of the parent strain.

In accordance with this discovery, it is an object of the invention to select and isolate the novel strains pursuant to mutagenesis of the wild type.

It is also an object of the invention to cultivate the mutant strains on a nutritionally sufficient sporulation medium in order to induce the formation of parasporal crystals.

A further object of the invention is to recover substantially spore-free entomocidal products from the media of the cultivated strains.

Other objects and advantages of this invention will become readily apparent from the ensuing description.

DETAILED DESCRIPTION OF THE INVENTION

The novel mutant microorganisms of this invention have been derived from a single parent strain of *B. thuringiensis* subsp. kurstaki NRRL B-3792 (HD-1) according to a procedure adapted from the method of Adelburg et al. [Biochem. Biophys. Res. Commun. 18: 788–795 (1965)] for mutating *Escherichia coli*. The mutagen used in this procedure is N-methyl-N'-nitro-N-nitrosoguanidine (MNNG) which typically induces death to approximately 95-98% of the cultured bacteria. Upon plating, a percentage of the survivors produce colonies with translucent or less pigmented sectors. From such sectors, oligosporogenic mutants that retain the ability to form parasporal crystals are isolated and then streaked until pure. The terms "oligosporogenic" and "oligosporogenous" are used herein in reference to the condition of producing an abnormally small number of spores. Selection of the instant mutants in accordance with this procedure is described in detail in Examples 1 and 2 below.

EXAMPLE 1

*B. thuringiensis* subsp. kurstaki NRRL B-3792 (HD-1) was cultured overnight at 30° C. on NSMP medium having the following composition:

|  | grams/liter |
| --- | --- |
| Casamino acids (Difco) | 5.0 |
| glucose | 2.0 |
| $KH_2PO_4$ | 0.932 |
| $K_2HPO_4$ | 0.549 |
| sodium citrate | 0.588 |
| $MgCl_2 . 6H_2O$ | 0.2033 |
| $CaCl_2 . 2H_2O$ | 0.1029 |
| $MnCl_2 . 4H_2O$ | 0.0099 |
| $ZnCl_2$ | 0.00068 |
| $FeCl_3$ | 0.00016 |
| distilled $H_2O$ | 1000 ml. |
| pH | 6.5 |

The culture was then reinoculated onto fresh NSMP medium and incubated at 30° C. for 4 hours. After the incubation, the cells in their exponential phase of growth were washed aseptically by centrifugation twice with saline (0.87% NaCl) and resuspended in 10 ml. saline in a sterile 50-ml. flask. Ten milliliters of 0.2% solution of MNNG were added to the flask for a final concentration of 1 mg. MNNG/ml. This resulted in an approximate kill rate of 99.9%. After incubation on a water bath shaker for 30 minutes at 30° C., the suspension was washed by centrifugation twice with sterile saline and resuspended on 50 ml. of fresh NSMP growth media. At the end of 4 hours of incubation, the culture was serially diluted in 0.1% tryptose broth dilution tubes and 0.1 ml. was spread onto NSMP agar plates which were incubated for 2-3 days at 30° C. Colonies were screened for sporeless mutations by microscopic examination and visual selection of lighter, less-pigmented sectors. Three oligosporogenous, crystal-producing isolates (1A1, 1A2, and 1A3) were selected and each was restreaked until pure and stable.

EXAMPLE 2

The mutagenesis procedure of Example 1 was repeated except that 10 ml. of 0.02% MNNG was used for a final broth concentration of 100 μg./ml. and the kill rate was approximately 99.6%. Three oligosporogenous, crystal-producing isolates (2A71, 2A72a, and 2A72b) were selected and each was restreaked until pure.

The mutant strains isolated from Examples 1 and 2 above have been deposited in the Agricultural Research Culture Collection (NRRL) in Peoria, Illinois, and have been assigned the following accession numbers:

| | |
|---|---|
| 1A3 | NRRL B-4453 |
| 2A72a | NRRL B-4454 |
| 1A1 | NRRL B-4455 |
| 1A2 | NRRL B-4456 |
| 2A71 | NRRL B-4457 |
| 2A72b | NRRL B-4458 |

While individual taxonomic characterizations were not developed for each of these strains, it is presumed that they possess substantially the same characteristics as the wild type, with the exception of their sporulation capacity. All six isolates are similar in morphological appearance when viewed with a phase microscope. Refractile spores are not visible, but indications of aborted sporulation are apparent in the form of phase-darkened bodies in polar regions and asymmetrical septum formation. All isolates produce large crystals, occurring either singularly or in multiples per cell, and as in the parent strain, they oftentimes are somewhat asymmetrical in shape.

Electron microscopy of thin sections taken from 24-hour-old preparations reveals that all six isolates are blocked at stage II of sporulation or before. In many instances, no spore-related structures are observed; in others, a sporulation septum is visible; and in some, complete engulfment of the forespore has occurred. Visible evidence of cortex synthesis is lacking. Parasporal crystals are generally tetrahedral in shape, but fractures and surface irregularities are often visible. Thin sections of free crystals are characterized by numerous surface irregularities and protrusions, much like the embedded bodies described by Sharpe and Baker [J. Invertebr. Path., in press (1980)]. Removal of the embedded body leaves concavities or depressions in the crystalline surface. Repeating regularly spaced lattice fringes at the edges of the crystal, indicative of the internal hexagonal array of crystalline subunits that comprise the fully formed paraspore, are also apparent in thin-section high-magnification micrographs.

In the production of a parasporal product by any of the oligosporogenic mutants, any known solid or liquid sporulation medium normally used for producing spores and crystals by cultivating the wild-type *B. thuringiensis* may be employed. The NSMP medium described above for use in the mutagenesis procedure is well suited for this purpose. Of course it is understood that the production of spores will not be positively influenced by the medium beyond the sporulation capability of the mutant cells.

The cultivation conditions are typical of those employed for sporulation of the wild type. Thus, for optimum production, temperatures will be on the order of 30° C. and incubation periods will be from about 2 to about 5 days. However, since viability of the isolates diminishes rapidly after 8 hours, maintenance cultures must be incubated no longer than 8–10 hours and stored immediately thereafter for preservation.

The crystals may be recovered from the culture medium by any conventional procedure known in the art. Washing with centrifugation separates the crystals and cellular debris from the liquid components of the medium resulting in a crude parasporal product. Since the mutant strains are characterized by a low sporulation rate, this crude product will be substantially free of spores suitable for most commercial applications. If desired, the cellular debris can be easily removed using buoyant density centrifugation. For a more refined preparation, the solids may be resuspended in 1 M NaCl and held at about 37° C. until the nucleoprotein derivatives are denatured. After additional washing, final isolation of a pure parasporal fraction completely devoid of spores is readily accomplished by linear gradient centrifugation. The initially reduced number of spores eliminates overloading of the gradients with its consequent overlapping of the spore and crystal bands.

The percent sporulation for cultures of the novel mutant strains is typically between about 0.01% and 0.13% without significant loss of crystal yield. Therefore, the spore-crystal ratios are in the range of from about 1:800 to about 1:8000. For purposes of this invention, crystal preparations having a spore count within this range are considered to be substantially spore-free. Actual spore counts are illustrated in Example 3 below.

EXAMPLE 3

*B. thuringiensis* subsp. kurstaki parent strain NRR1 B-3792 and the six mutant strains obtained in Examples 1 and 2 were cultivated on NSMP medium in 50-ml. shake flasks at 30° C. for 24 hours. After samples from each culture were plated for viable counts of vegetative cells, aliquots of the cultures were heated at 80° C. for 12–15 minutes to kill the existing vegetative cells. Samples were then plated to ascertain the spore count of each culture. The results are shown in Table I below.

TABLE 1

| Strain (NRRL) | Viable count (vegetative cells/ml. culture) | Spore count (spores/ml. culture) | % Sporulation |
|---|---|---|---|
| B-3792 (parent) | $8 \times 10^7$ | $7.5 \times 10^7$ | 93.8 |
| R-4453 | $6.8 \times 10^6$ | $4.5 \times 10^3$ | 0.066 |
| B-4454 | $1.6 \times 10^7$ | $2.1 \times 10^3$ | 0.013 |
| B-4455 | $8 \times 10^6$ | $5 \times 10^3$ | 0.063 |
| B-4456 | $6 \times 10^6$ | $7.4 \times 10^3$ | 0.123 |
| B-4457 | $5 \times 10^6$ | $1 \times 10^3$ | 0.020 |
| B-4458 | $8 \times 10^6$ | $4.3 \times 10^3$ | 0.054 |

The toxicity of the parasporal proteins isolated from the various mutant strains appears to be comparable to or better than that of the wild-type δ-endotoxin. This fact has been established by data from in vitro bioassays conducted in accordance with the procedure set forth in Example 4, below.

EXAMPLE 4

A. Preparations containing crystals and cellular debris resulting from growth of the parent and the six isolate strains of Examples 1 and 2 on agar plates or in shake flasks were washed twice by centrifugation with 10 ml. tris (hydroxy-methyl) aminomethane (Tris), pH 7.8, and 0.05 M KCl. Washed pellets were resuspended in 1 M NaCl and heated at 37° C. for 18 to 24 hours to hasten the removal of nucleoprotein derivatives from the vegetative debris. The suspensions were then centrifuged and the pellets were given four more washes in saline solution at 37° C. The resulting pellets were then resuspended in a small volume of 1 M potassium thiocyanate (KSCN) and placed upon a linear gradient of 40–80% sodium diatriazoate (either "Hypaque Sodium" or "Renografin"). The gradients were centrifuged at 8000 x g. for 2 hours. The crystals concentrated in a band two-thirds of the way down the tube, with most cellular debris retained diffusely throughout the upper part of the gradient. Crystals were collected, washed in buffer, and reseparated on fresh gradients for a total of three passages through sodium diatriazoate. The resulting crystal preparations were free of contamination from spores or cellular debris.

B. To prepare the purified crystals for bioassay, the parasporal protein was first solubilized by suspension in 0.2 M sodium thioglycollate in 0.1 M sodium bicarbonate buffer, Ph 9.5, at 30° C. for 2 Hours. The resultant protein solution, or protoxin, was dialyzed overnight against 10 mM Tris, pH 8.5, 1 mM sodium thioglycollate, and 1 M KSCN. Solubilized parasporal protein solutions were adjusted to an approximate protein concentration of 5 mg./ml. and activated by enzymatic digestion with α-chymotrypsinogen A (bovine pancreas) at a level of 200 μg. enzyme/ml. of soluble parasporal protein. Millimolar quantities of $Ca^{++}$ and $Mg^{++}$ were added to the solubilized mixture to aid enzymatic digestion, which was conducted at 32° C. for 4 hours in a reciprocating water bath.

C. Bioassays were performed by adding 0.1 ml. of the activated parasporal protoxin solution to 0.1 ml. of buffered insect saline (BIS) containing 1.5 to $2.0 \times 10^5$ FPMI-CF-1 cells from minced neonate larvae of *Choristoneura fumiferana* (spruce budworm) and incubating for 30 minutes at 28° C. The incubation was terminated by the addition of 2 ml. of boiling 0.05 M Tris buffer, pH 7.7, to each assay tube and boiling for an additional 10 minutes. Residual adenosine triphosphate (ATP) was measured with a Packard Tri-Carb liquid scintillation spectrometer by the luciferin-luciferase assay as described by Stanley and Williams [Anal. Biochem. 29: 381-392 (1969)]. This assay measures the ATP content of cultured insect cells after treatment with toxin. Undamaged cells retain normal levels of ATP, but affected cells lose ATP to the culture milieu. Hydrolytic enzymes such as ATPase lost from the same damaged cells quickly destroy free ATP. In practice, the maximum lethal response of cultured insect cells to parasporal protein averages 70–80% of the total cell population. Consequently, the decrease in assayed cell culture ATP, corrected by the method of Murphy [Science 194: 954-956 (1976)] for the number of resistant cells, is a measure of the amount of toxin added to the culture. $LD_{50}$ values (the dose lethal to 50% of the susceptible cells) were determined by this technique and are reported in Table II below.

TABLE II

| Strain (NRRL) | $LD_{50}{}^a$ |
|---|---|
| B-3792 (parent) | 13.4 |
| B-4453 | 10.3 |
| B-4454 | 4.5 |
| B-4455 | 10.5 |
| B-4456 | 8.1 |
| B-4457 | 7.0 |
| B-4458 | 6.3 |

$^a$μg. parasporal protein per ml. digest (containing $1-2 \times 10^5$ cultured insect cells)

It is understood that the foregoing detailed description is given merely by way of illustration and that modification and variations may be made therein without departing from the spirit and scope of the invention.

I claim:

1. A method of producing a *Bacillus thuringiensis* parasporal product substantially free of contaminating spores comprising culturing an oligosporogenic mutant of *Bacillus thuringiensis* subspecies kurstaki having the identifying characteristics of a strain selected from the group consisting of NRRL B-4453, NRRL B-4454, NRRL B-4455, NRRL B-4456, NRRL B-4457, and NRRL B-4458 on a nutritionally sufficient medium whereby the vegetative cells of said mutant culture produce spores and parasporal crystals in a spore:crystal ratio of less than about 1:800, and recovering said substantially spore-free parasporal product.

2. The method as described in claim 1 wherein the spore:crystal ratio is less than about 1:1600.

3. The method as described in claim 1 wherein said strain has the identifying characteristics of NRRL B-4454.

4. The method as described in claim 1 wherein said strain has the identifying characteristics of NRRI B-4457.

5. The method as described in claim 1 wherein said strain has the identifying characteristics of NRRL B-4458.

6. A biologically pure culture of an oligosporogenic mutant of *Bacillus thuringiensis* subspecies kurstaki having the identifying characteristics of a strain selected from the group consisting of NRRL B-4453, NRRL B-4454, NRRL B-4455, NRRL B-4456, NRRL B-4457, and NRRL B-4458 wherein said culture is characterized by the ability to produce a parasporal product substantially free of contaminating spores upon fermentation in a nutritionally sufficient medium.

7. A biologically pure culture as described in claim 6 wherein said strain has the identifying characteristics of NRRL B-4454.

8. A biologically pure culture as described in claim 6 wherein said strain has the identifying characteristics of NRRL B-4457.

9. A biologically pure culture as described in claim 6 wherein said strain has the identifying characteristics of NRRL B-4458.

* * * * *